(12) United States Patent
De Oliveira Garcia Da Fonseca et al.

(10) Patent No.: US 9,914,120 B2
(45) Date of Patent: Mar. 13, 2018

(54) BLOOD CELL COUNTING DEVICE AND METHOD

(71) Applicant: BIOSURFIT S.A., Aveiro (PT)

(72) Inventors: João Manuel De Oliveira Garcia Da Fonseca, Azambuja (PT); Ricardo Cabeça, Lisbon (PT)

(73) Assignee: Biosurfit S.A., Aveiro (PT)

( * ) Notice: Subject to any disclaimer, the term of this patent is extended or adjusted under 35 U.S.C. 154(b) by 536 days.

(21) Appl. No.: 14/384,200

(22) PCT Filed: Mar. 12, 2013

(86) PCT No.: PCT/EP2013/055020
§ 371 (c)(1),
(2) Date: Sep. 10, 2014

(87) PCT Pub. No.: WO2013/135713
PCT Pub. Date: Sep. 19, 2013

(65) Prior Publication Data
US 2015/0024426 A1    Jan. 22, 2015

(30) Foreign Application Priority Data
Mar. 12, 2012  (PT) .......................................... 106203

(51) Int. Cl.
*B01L 3/00* (2006.01)
*G01N 33/49* (2006.01)
(Continued)

(52) U.S. Cl.
CPC ...... *B01L 3/502753* (2013.01); *G01N 15/042* (2013.01); *G01N 15/05* (2013.01);
(Continued)

(58) Field of Classification Search
CPC ....... B01L 3/502753; B01L 2200/0605; B01L 2200/10; B01L 2200/16; B01L 2300/0654;
(Continued)

(56) References Cited

U.S. PATENT DOCUMENTS

2002/0076354 A1    6/2002  Cohen
2003/0083685 A1*   5/2003  Freeman ............ A61B 5/15146
                                                      606/181
(Continued)

FOREIGN PATENT DOCUMENTS

WO    WO 2003/104771 A1   12/2003
WO    WO 2006/042555 A2    4/2006
(Continued)

OTHER PUBLICATIONS

Berkel et al., "*Integrated Systems for Rapid Point of Care (PoC) Blood Cell Analysis*", © The Royal Society of Chemistry, Feb. 17, 2011, 8 Pgs.
(Continued)

*Primary Examiner* — Jonathan S Lee
(74) *Attorney, Agent, or Firm* — Patterson Thuente Pedersen, P.A.

(57) ABSTRACT

A device for use in imaging a liquid sample comprises an inlet for accepting the sample, a connection conduit and a detection chamber for detection of the sample, preferably optical detection of the sample. The connection conduit connects the inlet to the detection chamber and contains one or more dry reagents for reaction with the sample as the sample passes through the connection conduit. Specific embodiments include devices arranged for treating a blood sample, in particular lysing and staining the sample. The liquid flow may be driven by capillary effect. The device may further include liquid handling structures arranged for
(Continued)

centrifugally driven liquid flow, for example to meter a volume of sample and separate the sample into phases by centrifugation.

19 Claims, 12 Drawing Sheets

(51) Int. Cl.
| | | |
|---|---|---|
| *G01N 15/04* | (2006.01) | |
| *G01N 15/05* | (2006.01) | |
| *G01N 15/14* | (2006.01) | |
| *G01N 21/07* | (2006.01) | |

(52) U.S. Cl.
CPC ..... *G01N 15/1463* (2013.01); *G01N 15/1484* (2013.01); *G01N 21/07* (2013.01); *G01N 33/491* (2013.01); *B01L 2200/0605* (2013.01); *B01L 2200/10* (2013.01); *B01L 2200/16* (2013.01); *B01L 2300/0654* (2013.01); *B01L 2300/0803* (2013.01); *B01L 2300/0864* (2013.01); *B01L 2300/0867* (2013.01); *B01L 2300/0883* (2013.01); *B01L 2400/0406* (2013.01); *B01L 2400/0409* (2013.01); *B01L 2400/0688* (2013.01); *G01N 2015/045* (2013.01); *G01N 2015/055* (2013.01)

(58) Field of Classification Search
CPC ..... B01L 2300/0803; B01L 2300/0864; G01N 15/042; G01N 15/05; G01N 15/1463; G01N 15/1484; G01N 21/07; G01N 33/491
See application file for complete search history.

(56) References Cited

U.S. PATENT DOCUMENTS

| | | | | |
|---|---|---|---|---|
| 2003/0224395 | A1* | 12/2003 | Jovanovich | B01L 3/0241 |
| | | | | 506/16 |
| 2007/0178521 | A1* | 8/2007 | Sakaino | B01L 3/502753 |
| | | | | 435/7.1 |
| 2008/0002178 | A1* | 1/2008 | Ogawa | B01L 3/50273 |
| | | | | 356/39 |
| 2008/0212069 | A1* | 9/2008 | Goldberg | B01L 3/502761 |
| | | | | 356/36 |
| 2009/0185714 | A1 | 7/2009 | Lindberg | |
| 2009/0311675 | A1* | 12/2009 | Hosokawa | G01N 33/86 |
| | | | | 435/5 |
| 2009/0311796 | A1 | 12/2009 | Griss et al. | |
| 2010/0291588 | A1 | 11/2010 | McDevitt et al. | |
| 2011/0026009 | A1* | 2/2011 | Knutson | G01N 33/54373 |
| | | | | 356/39 |
| 2013/0130262 | A1* | 5/2013 | Battrell | B01L 3/50273 |
| | | | | 435/6.12 |
| 2013/0164778 | A1* | 6/2013 | Janisch | B01L 3/502738 |
| | | | | 435/39 |
| 2013/0302809 | A1* | 11/2013 | Bru Gibert | G01N 21/75 |
| | | | | 435/6.12 |
| 2015/0298118 | A1* | 10/2015 | Chard | B01L 3/50273 |
| | | | | 435/7.92 |
| 2016/0175836 | A1* | 6/2016 | Taylor | B01L 3/50273 |
| | | | | 435/287.2 |

FOREIGN PATENT DOCUMENTS

| | | |
|---|---|---|
| WO | WO 2006/070772 A1 | 7/2006 |
| WO | WO 2006/084472 A1 | 8/2006 |
| WO | WO 2009/037361 A1 | 3/2009 |
| WO | WO 2009/069656 A1 | 6/2009 |
| WO | WO 2010/120786 A1 | 10/2010 |
| WO | WO 2011/122972 A2 | 10/2011 |

OTHER PUBLICATIONS

Portuguese Search Report for Portuguese Application No. 106203, dated May 9, 2012, 8 Pgs.
PCT International Search Report for PCT/EP2013/055020, dated Jun. 11, 2013, 4 pgs.
PCT Written Opinion for PCT/EP2013/055020, dated Jun. 11, 2013, 5 Pgs.
Translation of Office Action dated Jan. 31, 2017 for Japanese Application No. 2014561423, 3 pages.

* cited by examiner

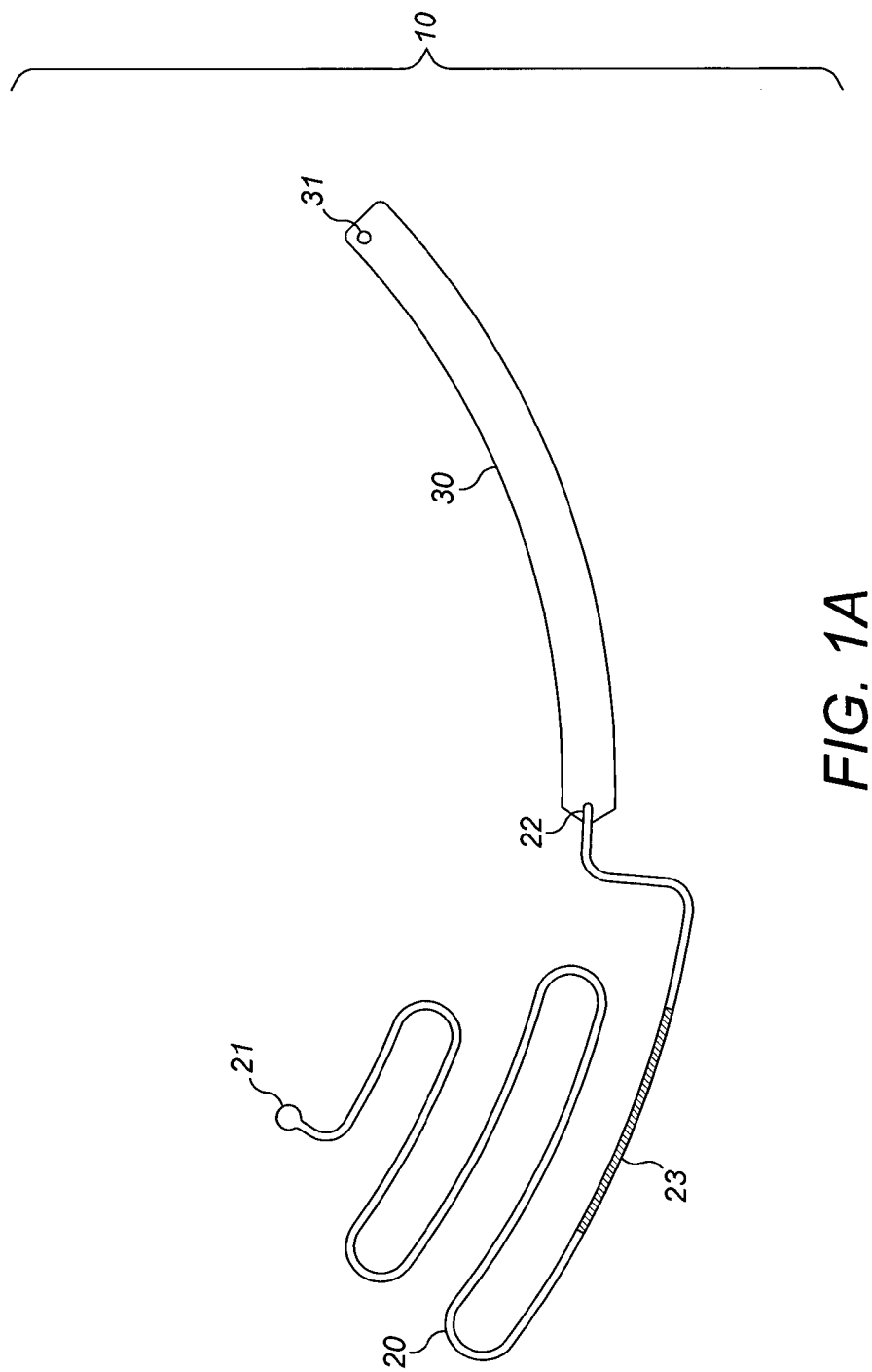

BLOOD CELL COUNTING DEVICE AND METHOD

RELATED APPLICATIONS

This application is a National Phase entry of PCT Application No. PCT/EP2013/055020, filed Mar. 12, 2013, which claims priority from Portuguese Application No. 106203, filed Mar. 12, 2012, the disclosures of which are hereby incorporated by referenced herein in their entirety.

FIELD OF THE INVENTION

The present disclosure relates to a device and method for use in testing a liquid sample, in particular although not exclusively performing blood cell counts on leukocytes and determining haematocrit fractions in a blood sample. More particularly, the device and method work with re-suspension of reagents, for example for lysis and staining, while blood flows into one or more detection chambers of the device.

BACKGROUND OF THE INVENTION

Devices which test blood are commonly known. Conventional systems are often expensive and therefore diagnostic testing often occurs at sites remote from the patient at centralised labs. This often results in significant delay in obtaining the results of a blood test.

To address this problem, devices and methods have been developed that offer point-of-care diagnostic testing. However, often these systems are expensive and the results obtained are often unreliable.

One such example of a device is described by Berkel C, et al, in "Integrated Systems for rapid point of care (PoC)". Although Berkel discloses that a Point of Care system is desired which provides test accuracy, quality control and cost-effectiveness, the disclosed system still suffers from numerous drawbacks. The system is only effective if timing and blood flow is closely monitored and concentrations are controlled precisely. Further, the system requires extensive training and specialised personnel to operate.

Therefore, here is a need for an enhanced device and method capable of providing fast, precise and affordable blood analysis taken at the point of case.

SUMMARY OF THE INVENTION

In a first aspect, there is provided a device for use in imaging a sample as set out in independent claim 1.

In some embodiments, the device comprises an inlet for accepting a sample into the device, a connection conduit and a detection chamber for optical detection of the sample. The connection conduit connects the inlet to the detection chamber and contains one or more dry reagents for reaction with the sample as the sample passes through the connection conduit. By providing for gradual resuspension, the method allows for a series of independent chemical reactions to process the sample as it flows through the cartridge.

In some embodiments, the conduit coated with the one or more reagents.

The sample may be a blood sample, and preferably the one or more dry reagents include a haemolysing agent for selective lysis of erythrocytes in the blood sample and a staining agent for selectively staining leukocytes in the blood sample. This allows for a tailored approach to counting populations of eutrophils, lymphocytes, monocytes, eosinophils and basophils.

In some embodiments, the connection conduit may comprise a main conduit portion and one or more protrusions extending outwardly from and along the main conduit portion. The dry reagents in this embodiment are stored in the one or more protrusions and respective junction regions between the one or more protrusions and the main conduit portion provide a reaction region in which gradual resuspension of the dry reagents can occur. The protrusions may further comprise a main portion and a neck portion in the region of the junction, the neck portion having a smaller cross-sectional area along the main conduit portion than the main portion.

Preferably, the connection conduit is of a meandering configuration. The cartridge can therefore be adapted into any desired shape to account for space requirements and constraints within the system.

Preferably, the device further comprises a stabilizer agent specific for leukocytes of the family of aldehyde-based fixatives, picric acid-based fixatives and polyoxyethylene-polyoxypropylene block copolymers stored in dry form in the connection conduit. Preferably, the connection conduit further comprises a surfactant in dry form. The haemolysing agent may be a saponin reagent. The staining agent may belong to the family of H&E stains, Romanowsky stains, methacromatic stains or any combination thereof.

The detection chamber may be confined between two parallel planar surfaces with the distance of no greater than 0.03 mm between the planar surfaces. Preferably, the connection conduit has a width of less than 2 mm, a length of above 10 mm and a depth between 0.02 mm and 1 mm.

Preferably, the inlet, the connection conduit and detection chamber are dimensioned such that the blood sample flows from the inlet through the connection conduit and detection chamber by capillary driven flow. At least one dimension of the connection conduit may be less than the smallest dimension of the inlet and at least one dimension of the detection chamber may be less than the smallest dimension of the connection conduit. By providing for flow driven by capillary effect, this means that no external means need to be present to drive the flow within the cartridge. However, it will be understood that an external pump to provide pressure driven flow of the sample from the inlet through the connection conduit and the detection chamber can be provided, additionally or instead.

In some embodiments, the device may further comprise a metering chamber arranged to hold a predefined volume of the sample, wherein the metering chamber is in fluidic connection with the inlet and the connection conduit. In this embodiment, the device also comprises a split feature arranged between the metering chamber and the connection conduit to split the sample between the metering chamber and the connection conduit, and a downstream chamber in fluidic connection with the metering chamber and arranged to receive the predefined volume of the sample. Flow into the downstream chamber may be driven by centrifugal force due to rotation of the device about an axis of rotation, in some embodiments. A vent is provided on either side of a liquid inlet into the downstream chamber.

Preferably, the device further comprises an overflow chamber in fluidic connection with the downstream chamber and further comprising a siphon in fluidic connection with the downstream chamber. The inlet of the siphon is arranged radially inwards from a portion of the downstream chamber such that when the device is subjected to a centrifugal force once the siphon is primed, a predetermined volume of the sample is siphoned from the sample in the downstream chamber. This allows for accurate siphoning which is particularly advantageous when the sample is a blood sample as it enables plasma to be accurately siphoned off from the blood sample.

The device may further comprises an air channel network, wherein the air channel network comprises an air vent opening and an air channel network to connect one or more of the chambers of the device to the exterior of the device. This advantageously avoids the risk of overpressure from occurring within the device. This air channel network may be connected to a waste chamber which receives the overflow from the detection chamber for example due to a centrifugal force. The air channel network may be open to atmosphere outside the device to facilitate sample introduction and may be sealable to prevent sample spillage during rotation of the device. Once sealed, the air channel network may provide a closed vent circuit allowing pressure equalisation between chambers and other liquid handling structures of the device.

Preferably, dry anticoagulant may be stored in the metering chamber to prevent the blood from clotting. Optionally, the metering chamber may further comprise a surface tension barrier arranged to stop capillary driven flow between the metering chamber and the downstream chamber. The surface tension barrier is preferably arranged to enable liquid flow past the barrier when the device is rotating at more than a predetermined angular velocity relative to the axis of revolution and to prevent flow otherwise. Preferably, the volume of the downstream chamber is smaller than the volume of the said metering chamber so that some of the same overflow into an overflow chamber. This enables accurate metering.

In some embodiments, the device further comprises a waste chamber. The waste chamber is in fluidic connection with the detection chamber and is arranged radially inward from the detection chamber to receive centrifugally driven overflow from the detection chamber. The waste chamber the fore prevents clogging of the vent circuit, as it allows excess liquid from the sample in the detection chamber to escape in a controlled manner, therefore acting as an extension or expansion vessel. The vent chamber may be provided in series with the vent network, or connected parallel to it. Preferably, a surface-tension barrier further reduces the risk of uncontrolled liquid spillage into the vent circuit in the former case.

The device may be provided as a cartridge, for example a disc-shaped cartridge, preferably having a feature for engaging a drive mechanism.

In a second aspect, there is provided a system for imaging comprising the above device as set out in independent claim 17.

In some embodiments, the system further comprises imaging means for acquiring at least one image of the sample in the detection chamber.

The system may further comprise a drive for rotating the device about an axis of rotation. The features in the device are preferably arranged about the axis of rotation such that when the drive for rotation is in use, the liquid is driven through the device by centrifugal force.

The system may further comprise an external pump to provide pressure driven flow of the sample from the inlet through the connection conduit and the detection chamber.

The system may further comprise a processor configured to capture at least one image of the sample in the detection chamber. When the sample is blood sample, the at least one image taken by the processor will show the lysed and stained blood. The processor may further be configured to determine the haematocrit fraction in the downstream chamber and/or in the overflow chamber. By determining the fraction in both the downstream and overflow chamber, the system may ensure that the results are independent of flow into the overflow chamber.

The drive for rotating the device about an axis provides a centrifugal force which causes a two-phase separation of the blood sample in the downstream and overflow chambers into sedimented erythrocytes and blood plasma supernatant. The distance relative to the axis of revolution of the separation of the sedimenting erythrocytes and blood plasma within both the downstream and overflow chambers may be measured by the means of optical image acquisition as a function of time. The length of each of the blood plasma and erythrocyte enriched phases may also be measured in the radial direction relative to the axis of revolution as a function of time.

In a third aspect, there is provided a method for imaging a sample as set out in independent claim 18.

The method comprises the steps of inserting a sample into a first chamber or inlet of a cartridge and causing the sample to flow by capillary action from the first chamber through a connection conduit into a detection chamber. While the sample flows through the connection conduit one or more dry reagents are re-suspended. The method also comprises capturing at least one image of the sample in the detection chamber. By providing for gradual resuspension, the method allows for one or a series of independent chemical reactions to process the sample as it flows through the cartridge.

When the sample is a blood sample, the one or more dry reagents may include a haemolysing agent for selective lysis of erythrocytes in the blood sample and a staining agent for selective stain of leukocytes in the blood sample. This allows for a tailored approach to counting subpopulations of eutrophils, lymphocytes, monocytes, eosinophils and basophils.

Some embodiments include performing image cell segmentation and classification of leukocytes by comparison of obtained images of the lysed and stained blood in the detection chamber with pre-defined image properties thresholds. The method may further comprise the step of determining the haematocrit fraction by optical imaging measurement of the interface between packed red cells and blood plasma in a downstream chamber and, preferably, any overflow chamber connected to the downstream chamber. This improves the reliability of the blood count obtained by the method.

Preferably the step of filling a blood metering chamber with blood is done by capillary action. The first chamber and the blood metering chamber may be filled from a common inlet. The method may also further comprise the step of rotating the sensing cartridge such that the blood comprised in the metering chamber is moved by centrifugal force from the said blood metering chamber into a downstream chamber.

Preferably, the method may further comprise extracting from the downstream chamber a predefined volume of blood plasma for further analytical purposes. This method therefore allows the blood sample to be further analysed in an integrated manner.

BRIEF DESCRIPTION OF THE DRAWINGS

Embodiments are now described by way of example only to illustrate aspects and principles of the present disclosure, with reference to the accompanying drawings in which:

FIG. 1A illustrates a device for measuring differential leukocyte counts in a detection region;

FIGS. 2B to 2I illustrate the various phases of measuring differential leukocyte counts using the device of FIG. 2A.

DETAILED DESCRIPTION OF THE DRAWINGS

Figure 1B:
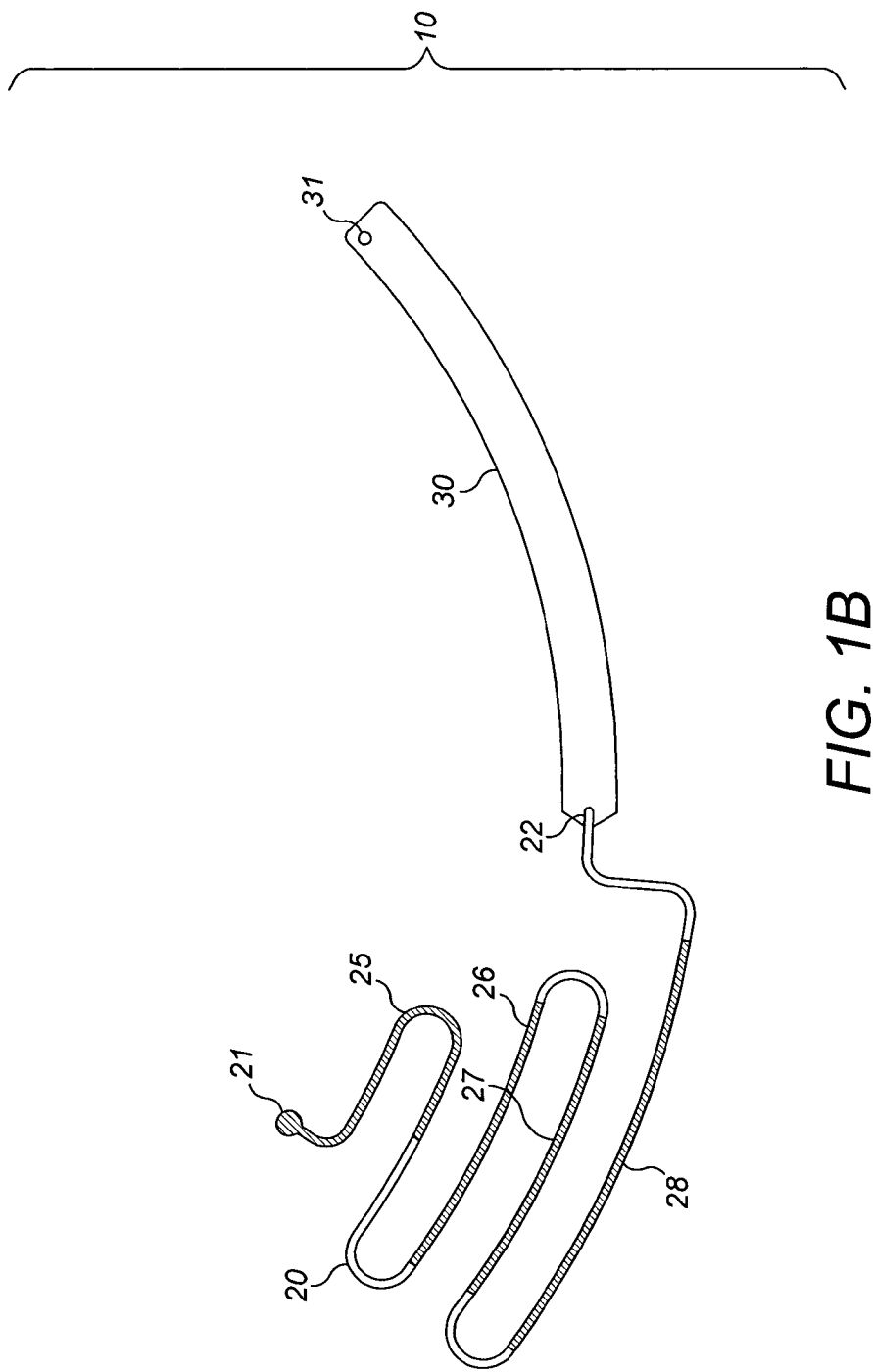
FIG. 1B illustrates a method for differential leukocyte counts in a detection region.

Herein described are miniaturized assemblies for blood sample handling and processing which provide integrated haematology tests within the framework of lab-on-a-chip and point-of-care technology. Further described herein is a microfluidic embodiment wherein metering of a blood sample volume, measurements of haematocrit and erythrocyte sedimentation velocity, absolute and differential count of leukocyte sub-populations and blood plasma extraction and aliquoting are combined in the same device. Preferably, the assembly is such that extracted cell free plasma can be used downstream for immunoassay testing.

Also described herein is a device which allows for a series of independent chemical reactions to process a blood sample; preferably including erythrocyte lysis and leukocyte differential staining. A five-part differential classification of leukocytes may then be tailored for counting subpopulations of neutrophils, lymphocytes, monocytes, eosinophils and basophils. It will be appreciated that further counting of blood platelets may also be performed.

FIG. 1A illustrates a microfluidic device (10) which comprises the following main fluidic structure: a sample inlet (21), a connection conduit (20) and a detection chamber (30).

The loaded blood sample flows from the sample inlet (21) through the connection conduit (20) by means of capillary or pressure driven flow. The shape and length of the connection conduit (20) may be arranged in such a manner that enables space saving within the device, using a meandering configuration.

The trajectory of the connection conduit (20) is provided within a single plane of the device (10) (one example is a serpentine shape as depicted in FIG. 1A). It will be appreciated that although a planar serpentine shape is depicted in FIG. 1A, any shape suitable for providing a substantially planar trajectory of the blood flow within the device could be provided. It should be noted that sharp angles within the projected trajectory should be avoided to reduce impediments to sample flow and to prevent trapping of air bubbles inside the connection conduit (20) whilst the chamber is filing with the blood sample. This is particular preferably where the blood flow is capillary driven.

The blood sample exits the connection conduit (20) through a defined outlet (22) as illustrated in FIG. 1A. The blood sample then proceeds by filling the detection chamber (30); wherein preferably, the detection chamber (30) comprises a vent (31) for air escape. The detection chamber (30) comprises two planar and transparent surfaces suitable for optical imaging. It will be appreciated that although the depicted detection chamber (31) in both FIGS. 1 and 2 comprises two planar, transparent surfaces, alternative arrangements which allow for optical imaging may be provided. Preferably, the height of the detection chamber (30) may be set to be no greater than 30 μm so that a single layer of blood cells is accommodated within it to facilitate cell counting. However, the height of the detection chamber (30) is not restricted to this height.

Following standard prototyping strategies, the device (10) may result from two halves containing microfluidic structures. These may be assembled together by any suitable means, for example using a bonding technique. Prior to assembly, the connection conduit (20) may be adapted to store dry reagents at particular positions therein. The dry reagents will preferably be prepared outside of the device (10) in a volatile solution at a given concentration. The precise amounts and concentration of reagent will depend on the solubility of the reagent. Once the solution is prepared, a predefined volume of the solution will then be dispensed at a given position of the connection conduit (20). By means of evaporation, the reagent will then be deposited within the wetted area (23) of the connection conduit (20) as illustrated in FIG. 1A. This procedure may be repeated as many times as necessary depending on the desired amount of reagent for dry storage.

The volume and surface tension of the loaded solutions is preferably chosen to allow for a proper filling and confinement within the connection conduit (20) so that a well-defined patch of dry reagents with a predefined length can be placed in a well defined position within the connection conduit (20).

The connection conduit (20) accommodates at least two types of dry reagents; for example a haemolytic agent and a staining agent. The role of the haemolytic agent is to selectively lyse erythrocytes from the blood sample before the detection chamber (30) is completely filled. By avoiding having erythrocytes present in the detection chamber (30) when it is filled with the processed blood sample, misinterpretation caused by leukocytes counts and posterior classification is reduced.

Furthermore, a staining agent from the family of hematoxylin and eosin (H&E) stains, Romanowsky stains, methacromatic stains or any combination thereof can be used for differential staining of leukocytes. From combinations of colour information with morphological features like granularity, size, shape of the cell cytoplasm and nucleus, it is possible to obtain a portfolio of distinct signatures for each of the sub-populations under study.

Furthermore, a stabilizing agent is provided in some embodiments. The stabilizing agent may be of the family of aldehyde-based fixatives, picric acid-based fixatives and polyoxyethylene-polyoxypropylene block copolymers and may be included as a dry reagent in the connection conduit (20). Such stabilizers are used to preserve and impart robustness to the leukocyte membrane and overall cell structure.

A surfactant also be included as a dry reagent in the connection conduit (20) in some embodiments. The surfactant may be used to decrease the surface tension between the blood sample and the inner walls of the connection conduit (20). Other properties of surfactants such as its use as a dispersant, detergent and emulsifier may also be useful to improve the reaction between the blood sample and the dry reagents.

As illustrated in FIG. 1B, while filling the connection conduit (20) from the inlet, the blood volume (25) encounters a series of patches of dry reagents (26, 27, 28). Although in FIG. 1B three patches of dry reagents are provided, it will be appreciated that any number (one or more) patches may be provided within the connection conduit (20). As the blood sample flows over the one or more patches, it will wash and dissolve the reagent(s) which will gradually diffuse through the blood volume and prompt a chemical reaction. The dynamics of such reactions depends mainly on the blood flow rate and the length of the patch of dry reagent. The content of dry reagent stored in the connection conduit (20) and how easily it dissolves on blood will also have an effect on the dynamics.

It may be noted that the front of the flowing blood which reaches the dry chemical patch first is more likely to wash a greater extent of the dry reagent depending on its solubility and the presence of surfactants in the system. Consequently, the concentration of a dissolved dry reagent along the blood volume in the direction opposite to the flow is expected to decrease. Along the direction normal to the dry reagent deposition surface (i.e. the direction comprising the height of the connection conduit (20)), the concentration of the dissolved dry reagent is expected to homogenize faster. That being said, the volume of the detection chamber (30) may preferably be designed to match a predefined fraction of the volume comprised by the connection conduit (20) to ensure that within said fraction the processed blood exhibits characteristics which are as homogeneous as possible.

Furthermore, depending on how many reactions are meant to occur throughout the connection conduit (20), it will be appreciated that the number of patches, the chemical composition of their respective dry content, the blood flow rate and/or the connection conduit (20) volumetry can be adjusted to suit the particular application.

An advantage of separating the at least one reaction site (26, 27, 28) from the detection chamber (30) where optical based detection of the processed sample occurs, is that the area and height of the detection chamber (30) can be independently adjusted for proper detection of the stained leukocytes and further traces of the dry reagents involved in the serial reactions can be excluded from the field of view; for example avoided precipitates of the stain under use in the field of view. The height of the detection chamber (30) may be set so as to contain one layer of stained leukocytes and an area to accommodate sufficient processed blood volume to provide a significant statistical count of each leukocyte sub-population.

In a further example a device for simultaneous measurement of partial or total leukocyte counts and haematocrit estimation and blood plasma extraction for further analytical purposes is disclosed.

Figure 2A:
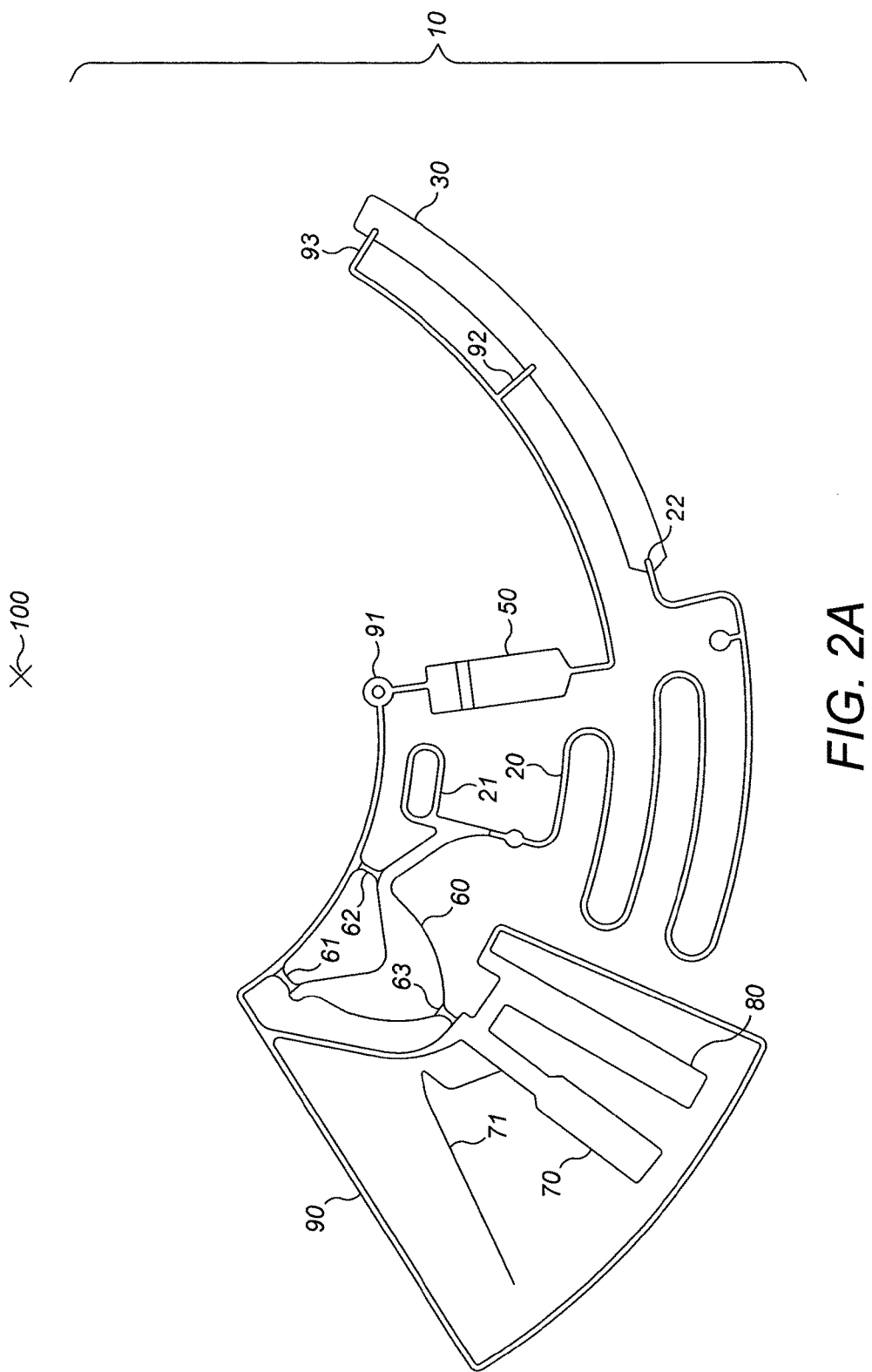
FIG. 2A illustrates a device for measuring differential leukocyte counts in a detection region and haematocrit determination and blood plasma extraction for further downstream processing.

The following microfluidic device comprises the main fluidic structures as represented in FIG. 2A: sample inlet chamber (21); connection conduit (20); detection chamber (30); waste chamber (50); metering chamber (60); downstream chamber (70); overflow chamber (80); network of air channels (90); flow barriers valves (61, 62, 63) and siphon (71). The network of air channels (90) assists with air exchange between all fluidic structures being filled with or emptied of the loaded blood sample, to provide a substantially even air pressure distribution in the device (10). The design of the microfluidic structures and their operation prevent sample ingress into the air channel network (90); otherwise under and overpressure regions may arise in the device (10) thereby compromising its fluidic functions.

The device (10) can be operated in two fluidic regimes: capillary driven flow and centrifugal pressure driven flow. Accordingly, the device may be designed to be rotatable about an axis of revolution (100) as illustrated in FIG. 2A to drive fluid flow by centrifugation.

All the fluidic structures described herein may be designed in polar coordinates relative to said axis of revolution (100). Consequently, all structures may be characterized by their radial and angular dimensions and positioning in respect of the axis of revolution (100). Upon rotation of the device (10) around the axis of revolution (100), a liquid sample in the device (10) experiences a centrifugal field.

Different volumes of a loaded blood sample may be metered and fractionated in independent aliquots for further independent processing. For hematologic tests it is desired that said blood aliquots have the same constitution and are representative of the loaded blood sample. Due to its complex biological composition, when a blood sample is exposed to a centrifugal field its components will redistribute themselves within the blood volume based on their densities, thereby jeopardizing the original homogeneity of the sample. The device (10) described herein and illustrated in FIG. 2 seeks to overcome or mitigate this issue.

Figure 2B:
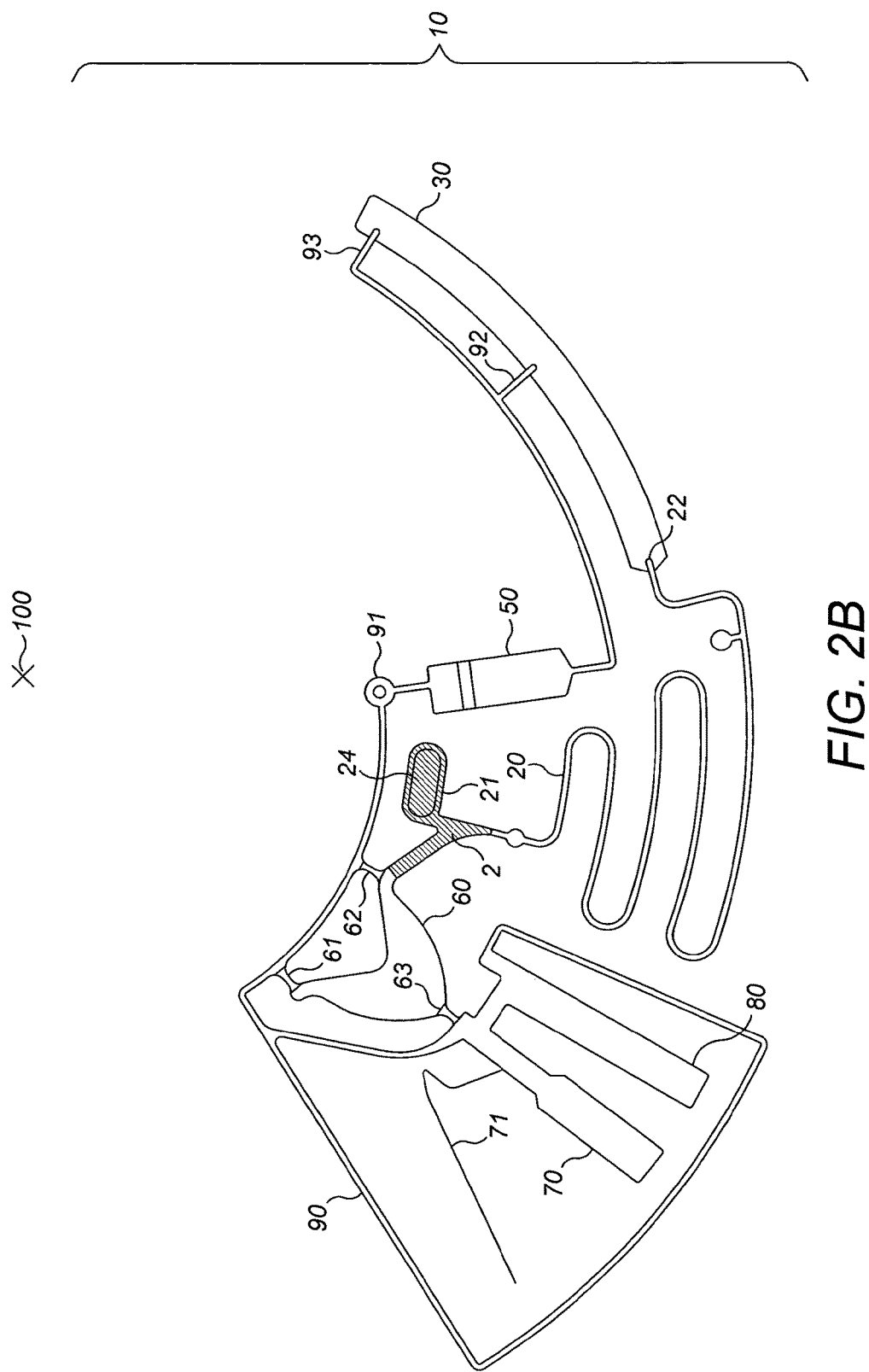

As illustrated in FIG. 2B, before loading the blood sample, the device (10) is exposed to atmospheric pressure through the open air vent (91) which is included in the integrated air channels network (90) which connects the fluidic modules listed above. The inlet chamber or sample inlet (21) comprises an opening (24) connecting the inlet chamber (21) to the exterior of the device (10). Once the sample is loaded into said opening (24), it moves into the inlet chamber (21) solely by capillary action and starts filling the chamber (21) towards the metering chamber (60) and connection conduit (20) simultaneously as is illustrated in the hatched section (2) in FIG. 2B.

Figure 2C:
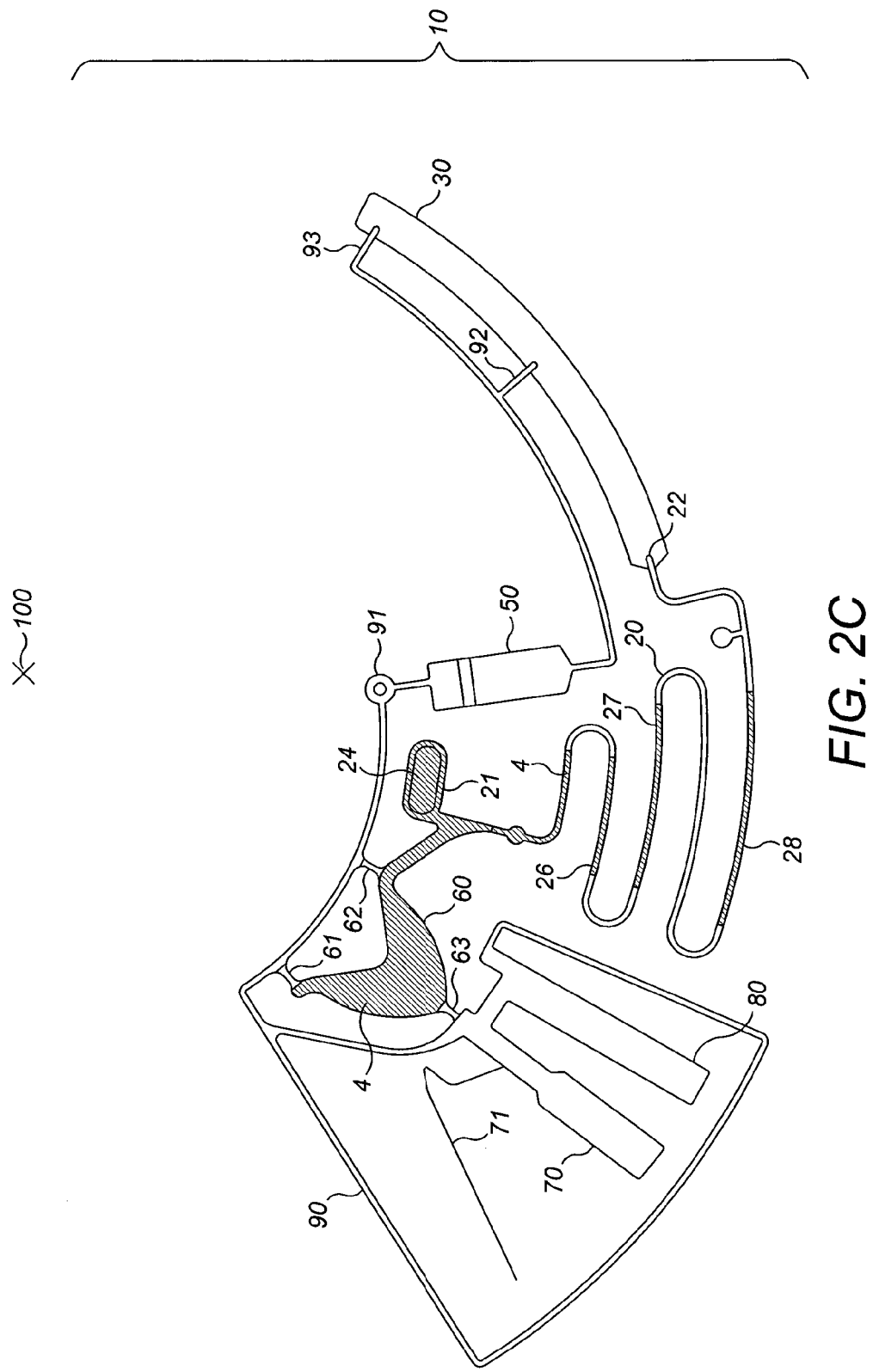

Meanwhile the metering chamber (60) substantially fills completely up to a predefined volume of the loaded blood sample. The metering chamber (60) is preferably shaped so to avoid entrapment of air bubbles while filling by capillary action as is illustrated in the hatched section (4) in FIG. 2C. One or more flow barriers valves are placed in the metering chamber (60) to connect the metering chamber (60) to the surrounding fluidic modules to ensure that the blood sample does not flow through the barrier valves by capillarity. As illustrated in FIG. 2C, the flow barrier valves (61, 62) are connected to the air channel network (90) to prevent clogging and ensure air release from the metering chamber (60) to the outside of the device (10). Providing an air release during capillary filling from one or more points of the metering chamber (60) enables complete filling of the chamber (60). Preferably, dried anticoagulant are additionally added to the metering chamber (60) to avoid undesirable clotting of the metered blood sample, in some embodiments.

Once the blood sample reaches the connection conduit 20 it fills it by capillarity as illustrated in the hatched section (6) of FIG. 2C. The chemical reactions operating on the blood whilst the blood sample is flowing over the dry chemical patches (26, 27, 28) comprised in the connection conduit (20) are as described above with respect to FIG. 1. Once the blood sample enters the detection chamber (30) by capillary, it has preferably already reacted with the erythrocyte lytic agent and differential stains for leukocytes.

The detection chamber (30) may include at least one connection to the integrated air channel network (90). Although two connections (92, 93) are illustrated in FIG. 2C, it will be appreciated that any number of connections may be provided.

Figure 2D:
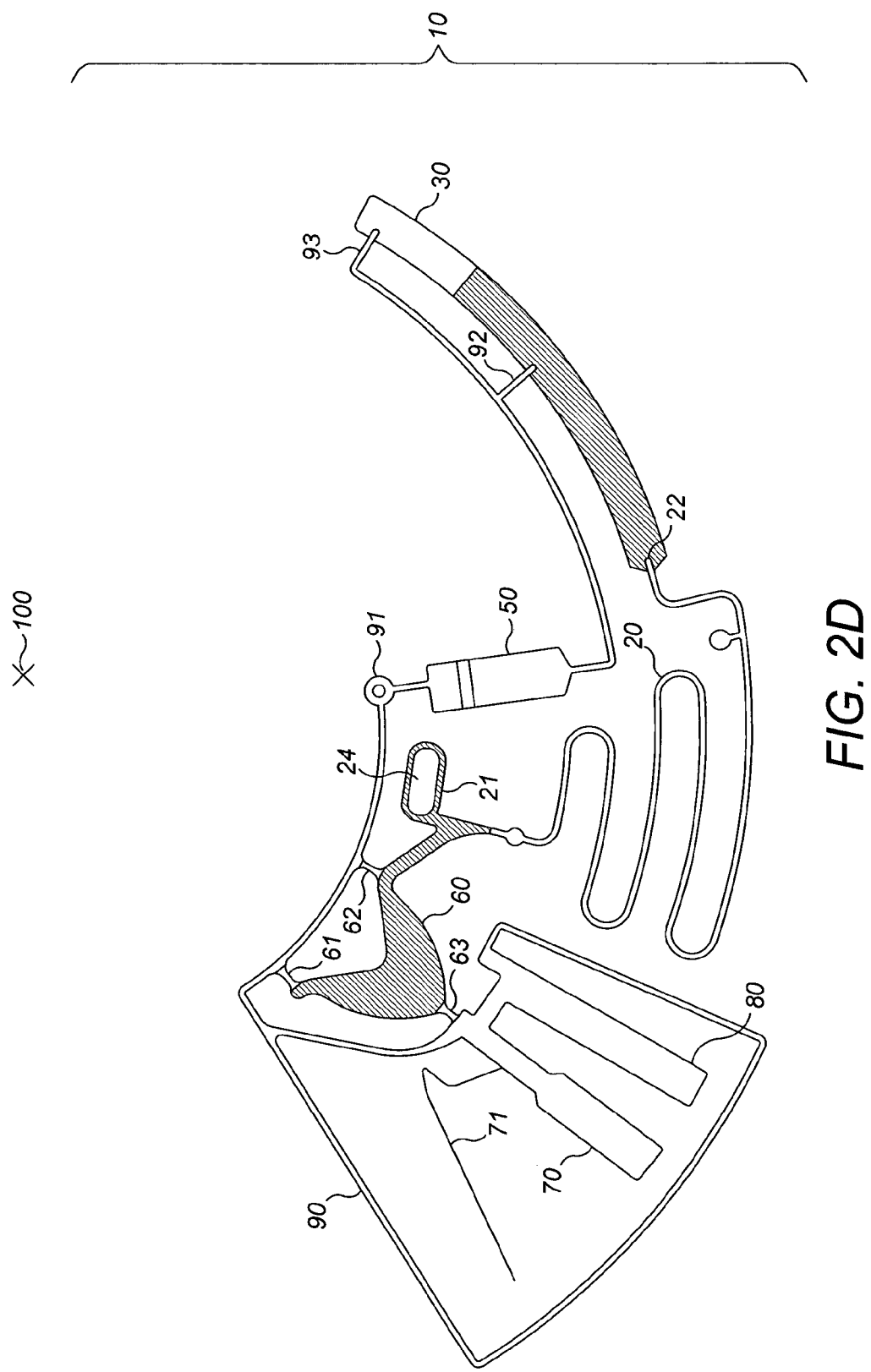

As illustrated in FIG. 2D, the connections (92, 93) allow air to escape while the detection chamber (30) is filled with the stained leukocytes sample, as illustrated in hatched section (8) in FIG. 2D. Each connecting air channel may include a flow barrier valve to prevent the processed blood volume from entering the air channels by capillarity. The air channels connect the detection chamber (30) to a waste chamber (50) located radially inwards on the device (10) relative to the axis of revolution (100). The role of the waste chamber (50) will be described in more detail below.

Figure 2E:
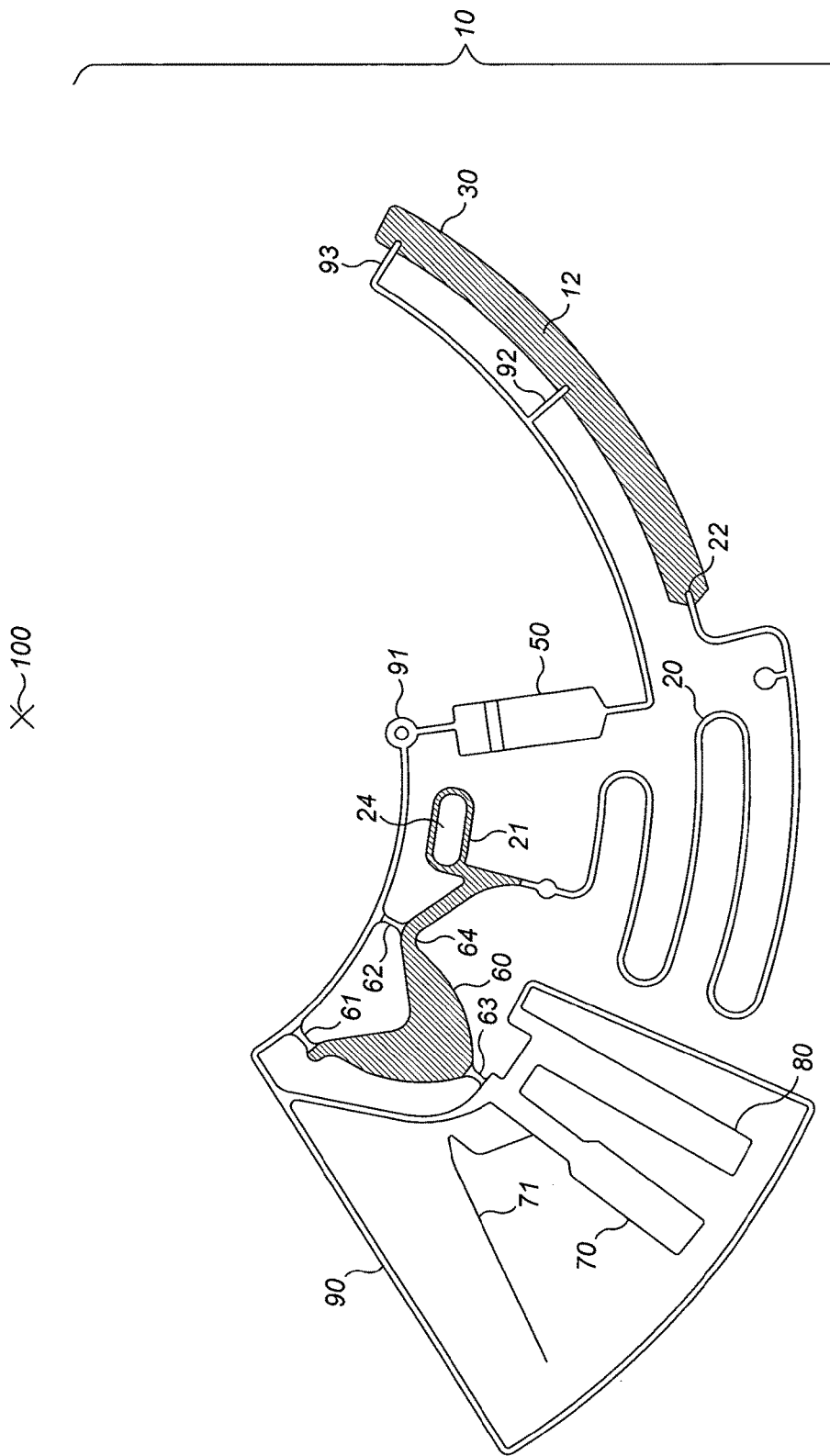

Once the detection chamber (30) is substantially filled with the blood sample, as illustrated by hatched section (12) in FIG. 2E, the device (10) may be placed in an instrument comprising a microscopy assembly and a transport mechanism. The microscopy assembly (10) may include a lens, a focusing mechanism and a digital camera. The transport mechanism allows angular positioning of the device (10) to be controlled. A positioning sensor may be used to assist the precise alignment of one of the extremities of the detection chamber (30) with the microscopy assembly which may then be followed by incremental angular displacements defining a series of positions within the detection chamber (30). At each position a focused picture of the processed blood sample may be taken with a given magnification. Furthermore, a precise radial positioning mechanism can be coupled to the device (10) for radial scanning of the detection chamber (30). The device (10) may also be immobilized or slowly rotating for discrete positioning purposes and all fluidic functions may be accomplished by capillary based handling of the blood sample without further interference/ assistance.

As soon as filling of the metering chamber (60) and image acquisition of the stained leukocytes in the detection chamber (30) have been completed, the device (10) is preferably operated in centrifugal based flow. At this point the opening of the inlet chamber (21) and air vent escape (91) may be sealed and future blood sample and air exchanges occur exclusively inside the device (10). Once the device (10) starts rotating at a given angular velocity about the axis of rotation (100), the blood volume comprised in it experiences a centrifugal force pointing towards the outward radius forcing the blood sample to flow. The same instrument is used, in some embodiments, during the capillary flow, image acquisition and centrifugal flow phases.

The metering chamber (60) in some embodiments, includes a split feature (64) between the metering chamber (60) and the inlet chamber (21). The split feature (64) may be characterized by a narrower passage between metering (60) and inlet chambers (21) and preferably has a cuspidal like shape with a rounded edge. Once the centrifugal force is actuated, the blood volume occupying an inner radial position of the device (10) which is normal to the split feature (64) edge will break at this point thereby providing a well-defined volume in the metering chamber for further processing.

Figure 2F:
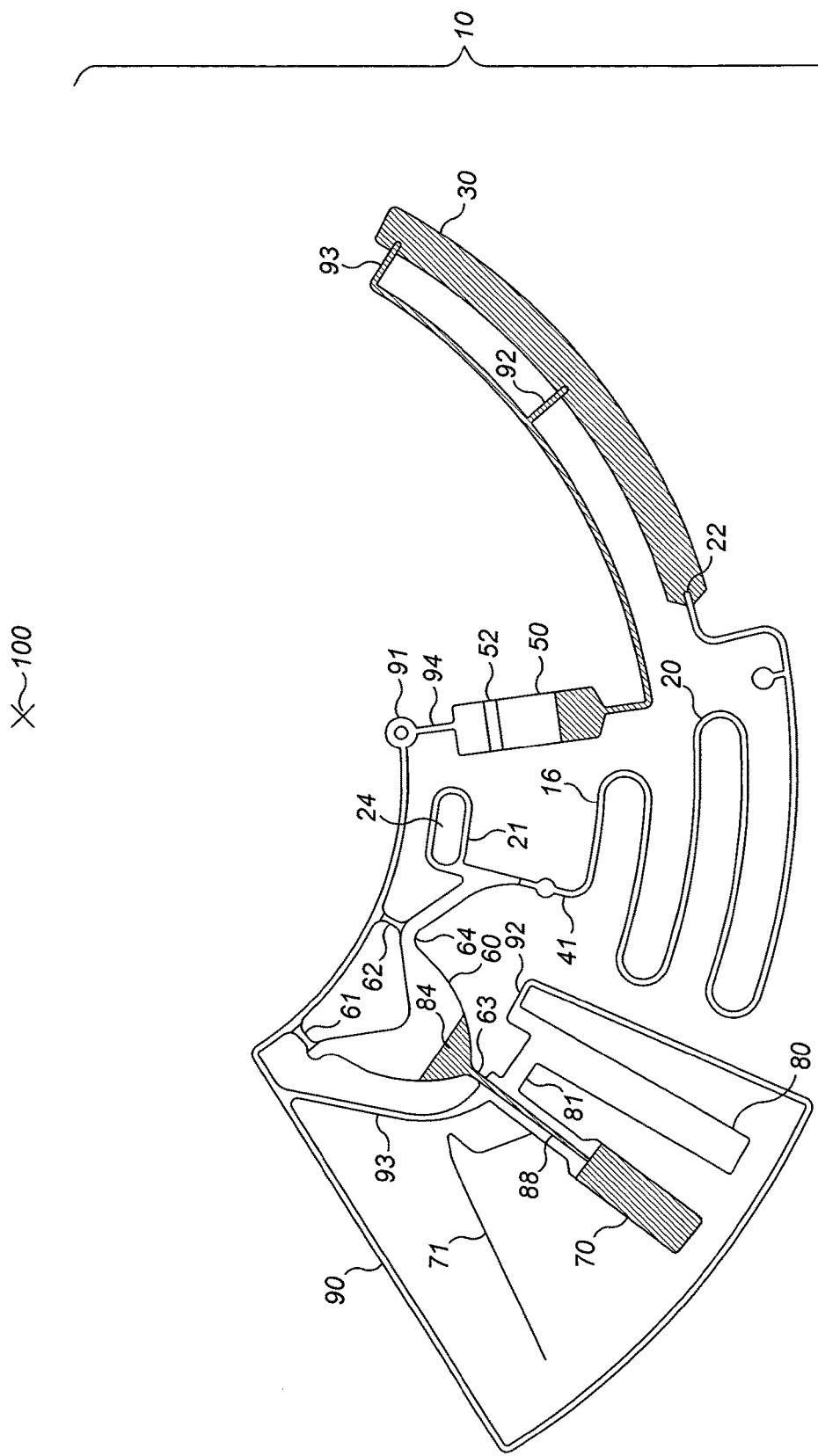
Figure 2G:
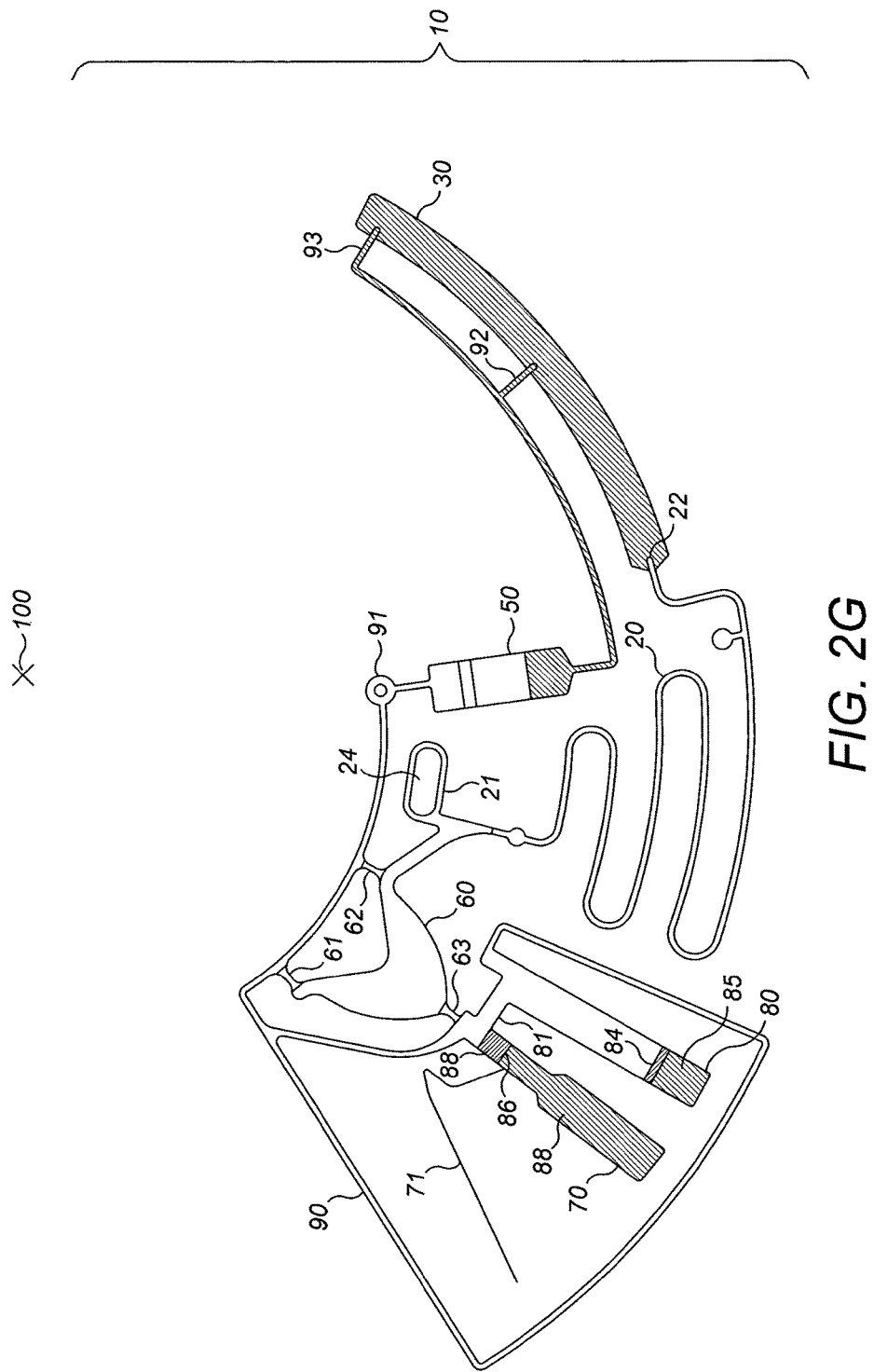
Figure 2H:
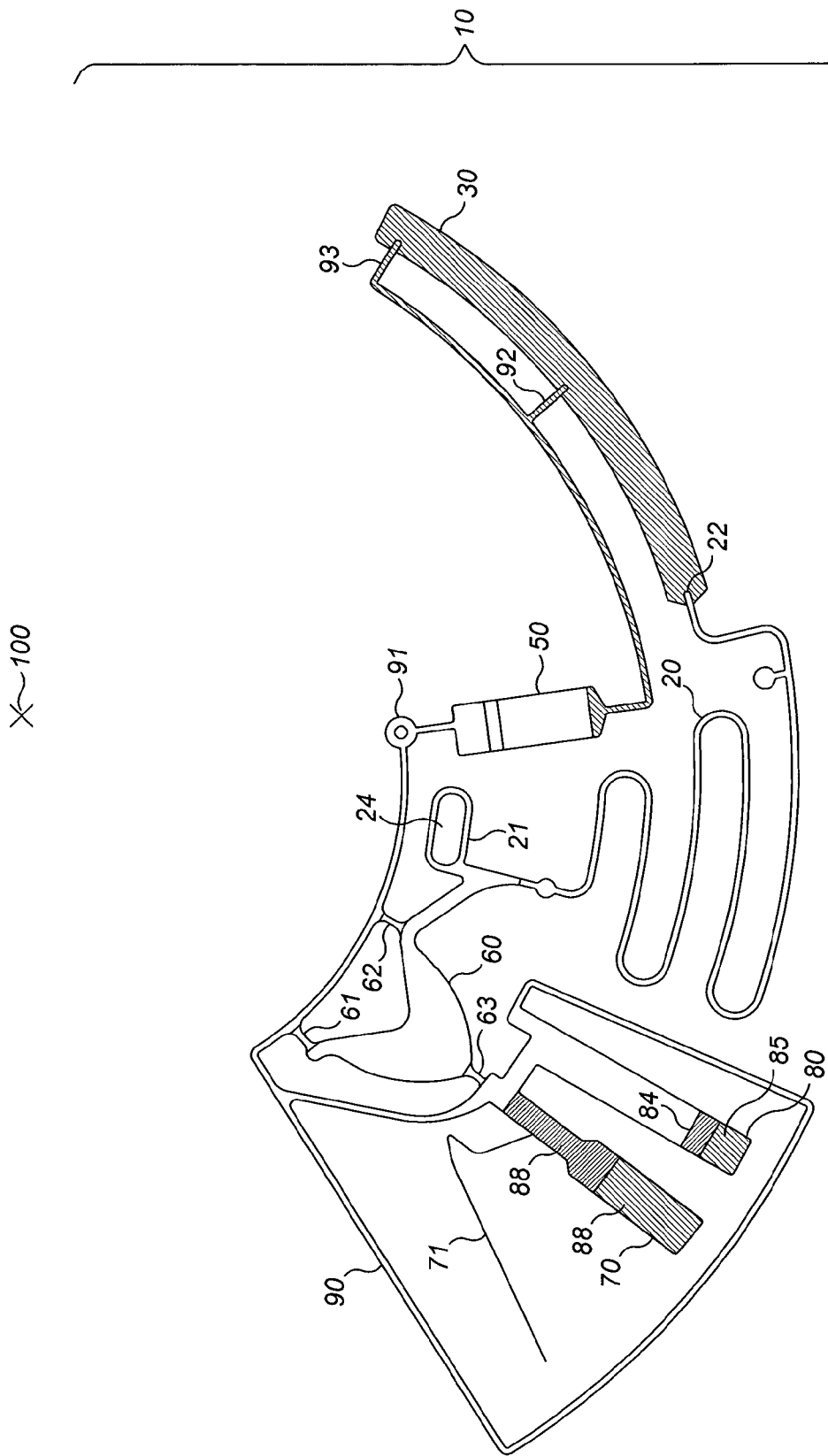
Figure 21:
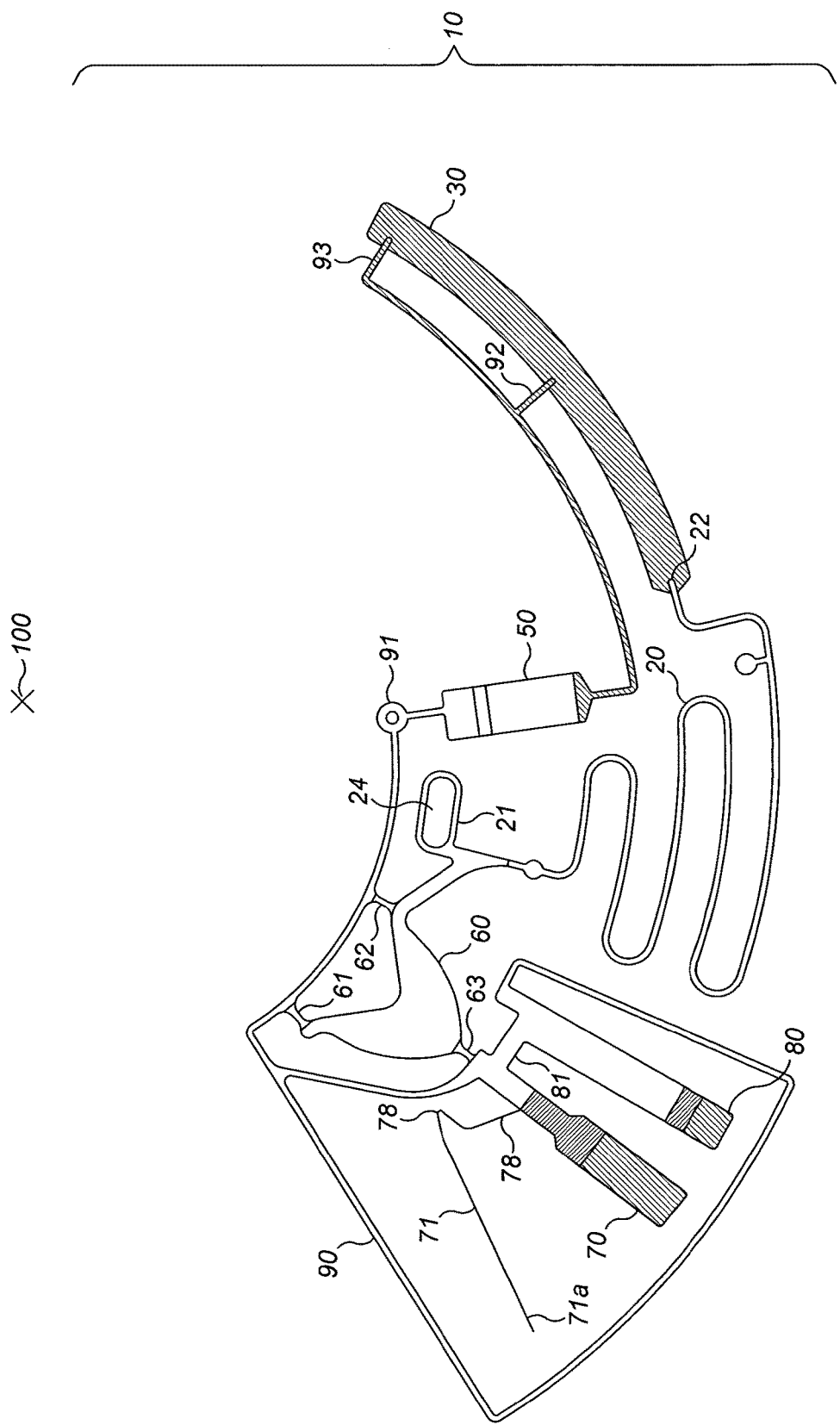
Figure 4:
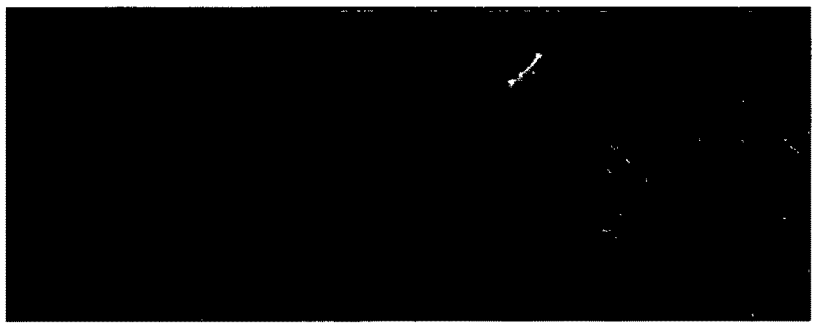
FIG. 4 is an image of a downstream chamber with packed red blood cells and blood plasma, according to the device and methods depicted in FIG. 1 or FIG. 2.

A flow barrier valve (62) is preferably provided which is connected to the air channel network (90) and may be aligned with the split feature (64) to prevent blockage and enable air ingestion which is needed for the blood sample split event as represented in FIG. 2F. The continuum of blood previously filling the device (10) will consequently divide into two independent fractions: the volume contained in the metering chamber (60) and the volume comprised in the inlet (21), connection conduit (20) and detection chamber (30) as illustrated by hatched sections (14) and (16) of FIG. 2F, respectively. The previous microfluidic architecture can be replicated in a series of n metering chambers (60) and n−1 split points between them to obtain n aliquots with predefined volumes from an initial blood sample.

The metering chamber (60) comprises at least one flow barrier valve (63) as illustrated in FIG. 2F, which connects the metering chamber (60) to a downstream chamber (70) and is located radially outwards with respect to the revolution axis (100). Upon rotation, the flow barrier valve (63) brakes given that the centrifugal force exerted on the metered blood volume is enough to overcome the surface tension barrier the valve (63) poses towards blood flowing through it. The braking events occurring at the split feature (64) embodied in the metering chamber (60) and the flow barrier valve (63) connecting the metering chamber (60) to the downstream chamber (70), is preferably synchronized for a correct fractionation of the blood volume enclosed in the metering chamber (60). Thereafter the metering chamber (60) is adapted to supply a substantially continuous stream of blood flowing from the flow barrier valve (63) into the downstream chamber (70) until it is substantially empty of blood, as is illustrated by grey out section (18) of FIG. 2F.

As illustrated in FIG. 2F, a stream of blood starts filling the outwardly radial positions of the downstream chamber (70) whilst the blood meniscus in said chamber (70) rises radially inwards until it reaches the connection (81) between the downstream (70) and overflow (80) chambers. A blood stream occupies the full height of the downstream chamber (70) as the downstream chamber is filled and consequently defines two fluidically separate areas extending from each side of the stream: 1) part of the downstream chamber (70) on the side of the siphon (71) and 2) its remaining volume plus the overflow chamber (80). Each of those areas is preferably connected to the air channel network (90) by one or more connections. As illustrated in FIG. 2F, two connections (92, 93) may be provided for air release while filling of the downstream chamber (70). This advantageously prevents overpressure which can arise within said areas. Overpressure can exert a deflecting force on the blood stream thereby risking incorrect filling of the downstream chamber (70).

The connection (81) between the downstream chamber (70) and the overflow chamber (80) is designed to transfer liquid in excess of a pre-defined volume enclosed in the downstream chamber (70) to the overflow chamber (80), which is preferably smaller than the metered blood volume, so that the overflow chamber (80) is partially filled with blood.

By such an arrangement, two independent fractions of the previously metered blood sample may be obtained. Furthermore, the presence of blood of this arrangement in the overflow chamber (80) may be used as a quality control to check the complete filling of the downstream chamber (70).

While filling both downstream (70) and overflow chambers (80), the metered blood sample is actuated by the centrifugal force as described above and consequently the erythrocytes contained in the sample will start to sediment. Even when filling of both chambers (70, 80) is accomplished, the device (10) is in some embodiments kept rotating for further sedimentation towards the outwardly radial positions of those chambers (70, 80). On further rotation, two respective erythrocyte depleted and enriched phases gradually appear on the blood volumes contained in the downstream (70) and overflow chambers (80) as is illustrated by hatched sections (32, 33) with respect to the downstream chamber (70) and hatched sections (34, 35) with respect to the overflow chamber (80), respectively.

The transition between the phases becomes more evident as sedimentation progresses. Image acquisition of the radial position of the interface between plasma and chamber material volumes in the downstream chamber (70) as a function of time may be used to measure the erythrocyte sedimentation velocity. The interface is illustrated by feature (36) in FIG. 2G. Once the sedimentation process is substantially completed a two phase blood sample with a sharp interface remains; one containing cell free blood plasma, the less dense fraction, radially inward and another containing the fully packed sediment of erythrocytes and other cellular material, the more dense fraction, radially outwardly. This is illustrated by hatched portions (37) and (38) in respect of the downstream chamber (70), respectively, and portions (39) and (40) in respect of the overflow chamber (80), respectively.

By means of image acquisition the extent of both fractions along the radial direction relative to the axis of revolution (100) can be measured. The ratio of these extents is a direct measure of the sample haematocrit. Said image acquisition routines may follow the description already mentioned for stained leukocyte imaging given that the magnification of the miniaturized optical microscope may be adjusted for a proper visualization of the plasma-erythrocyte phases and interface.

Haematocrit calculation is, in some embodiments, done by combining the measurements of both downstream (70) and overflow (80) chambers. The design of these chambers (70, 80), the rotation velocity of the device (10) and the rotation time are likely to influence both sedimentation and haematocrit measurements. It is important to note that until filling of the downstream (70) and overflow chambers (80) is substantially completed, the two phase separation of the flowing blood sample due to sedimentation already occurs. This implies that when the blood sample reaches the overflow level of the downstream chamber (70), the blood volume that flows towards the overflow chamber (80) is likely to be partially depleted from erythrocytes. Consequently, measurements of haematocrit on the downstream (70) and overflow (80) chambers reveal higher and lower haematocrit results, respectively. This is why haematocrit measurements on both chambers (70, 80) is preferable as it is likely to lead to a more accurate result.

In the same way, the haematocrit influences the erythrocyte sedimentation velocity measurements; the lower the haematocrit, the faster the sedimentation mechanism occurs. Again, the measured sedimentation velocity is preferably corrected to account for such bias.

The downstream chamber (70) may also include a siphon for cell free plasma (71) extraction once the erythrocyte sedimentation and haematocrit measurement are completed, as illustrated in FIG. 2I. When the blood sample filling the downstream chamber (70) reaches the inlet (78) of the siphon (71), it will partially fill and the meniscus of the blood volume contained in the siphon levels with the meniscus of the blood contained in the downstream chamber (70). As is illustrated in FIG. 2I, the siphon level is reached when the meniscus reaches the inlet level which is indicated by feature (81). This transition between the downstream chamber (70) and the overflow the chamber (80) is defined by a precise radial distance relative to the axis of revolution (100). To avoid untimely priming of the siphon (71) it is preferable that: 1) the siphon crest (79) is located radially inwards relative to the equilibrium radius; and 2) the centrifugal force acting on the blood volume contained in the siphon (71) overcomes the capillary force exerted on said blood volume which has the opposite direction of the centrifugal force in the siphon branch (77) comprised between its inlet (78) and crest (79).

When the device (10) stops rotating or rotates at a lower angular velocity such that the capillary force overcomes the centrifugal force, the blood volume progresses through the siphon (71) until priming is completed. It is preferable that the radial position of the blood volume inside the siphon (71) reaches a position in outer radius (79a) compared to the radius of the siphon inlet (78). At this point, the device (10) starts rotating and the cell free plasma comprised between the top of the downstream chamber (70) and the inlet (78) of the siphon (71) starts draining through the siphon (71).

The described preferable procedure ensures aliquoting of a precise volume of blood plasma given that said volume can be easily tuned by proper dimensioning of the downstream chamber (70) and location of the siphon inlet (78) in respect of the downstream chamber (70). To guarantee that the extracted plasma is not contaminated with erythrocytes, the siphon inlet (78) is preferably located above, or radially inwards, from the plasma-erythrocytes phase transition. Since such transition depends on the blood sample haematocrit, the siphon inlet (78) may be positioned for a sample with a haematocrit of up to 65% which is a value far above the maximum values found in practice. The aliquoted plasma volume can be further processed and used for additional testing.

The blood volume comprised in the inlet (21), connection conduit (20) and detection chamber (30) which is fractionated at the split feature (64), as is illustrated in FIG. 2F, is displaced under the influence of the external centrifugal force when the device (10) starts rotating. The meniscus defining the ends of blood volume preferably levels itself at the same radius to maintain the hydrostatic pressure independently of the shape and volume of the reservoirs filled in between, as illustrated by features (41) and (42) of FIG. 2F.

As a result of the levelling, the blood sample flows through the air channels (92, 93) towards the waste chamber (50). This happens where the rotation speed/centrifugal force overcomes the surface tension of the flow barrier valves embodied in said air channels (92, 93). Preferably, the fluidic structures are designed to ensure that the blood meniscus rises in the waste chamber (50) until it equilibrates with the meniscus on the other extreme of the blood fraction, which occurs below the split feature (64); i.e. on the outer radius relative to the axis of revolution (100). The radial position of the equilibrium of both meniscuses depends on the volume of the channels and reservoirs comprising the said blood.

This equilibrium radius preferably occurs below the surface tension barrier (52) disposed in the waste chamber (50). This barrier (52) ensures that once the microfluidic disc stops rotating, the blood in the waste reservoir (50) does not reach the air channels network (90) by capillary flow through channel (94), as illustrated in FIG. 2F.

In some embodiments, the device (10) as illustrated in FIG. 2A, is provided as a cartridge. The cartridge in some embodiment resembles a CD/DVD configuration constituted by two transparent and planar circular halves brought together by an intermediate adhesive layer. The halves are preferably engraved with the microfluidic structures and openings to the exterior described above, with the exception of the detection chamber (30) which is cut out from the adhesive layer. With precise alignment of the microfluidic structures, the three parts may be assembled and bonded to form a self-contained cartridge.

In one example, the connection conduit (20) is 30 mm long, 0.6 mm wide and 0.2 mm deep. This connection conduit (20) was tested for a series of 3 sequential reactions, comprising a first reaction site which was 10 mm long which comprised glutaraldehyde as a stabilizer agent, a 10 mm long reaction site with a mixture of surfactant and lytic agent (Surfynol and saponine, respectively) and a 10 mm long reaction site with a mixture of stains. In this example the mixture of stains included a mixture of eosin, methylene blue and basic orange 21 leading to differential colours for a 5-part classification of leukocytes: lymphocytes stain blue, monocytes stain blue/purple, neutrophils exhibit blue nucleus and pale yellow cytoplasm, eosinophils exhibit blue nucleus and dark yellow granules, basophils stain bright pink. It will be appreciated that other known reagents and combinations thereof may be used in the device. It will also be appreciated that the reagents may be arranged having different dimensions in the connection conduit (20).

Figure 3:
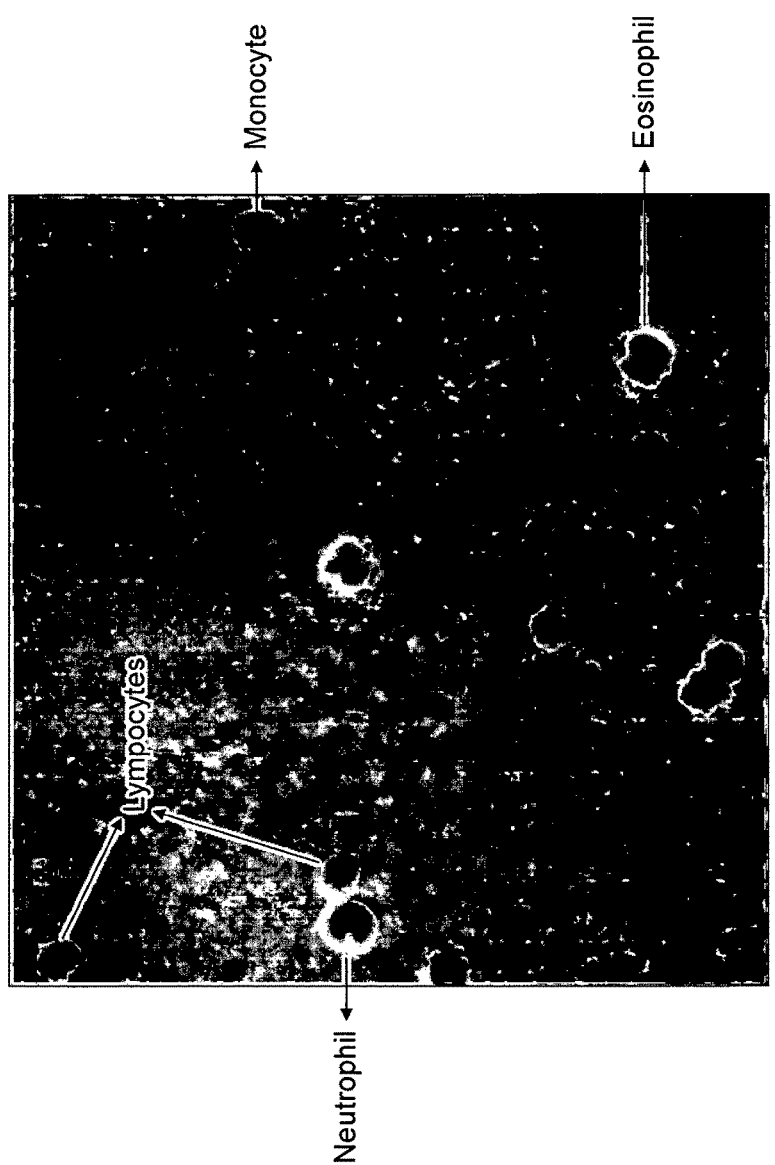
FIG. 3 is an image of lysed and stained blood in the detection region (40), according to the device and methods depicted in FIG. 1 and/or FIG. 2, wherein each type of leukocyte presents a distinctive optical imaging signature.

The configuration above defines a volume for the connection conduit (20) of 3.6 μL whereas the detection chamber (30) was designed to retain 1 μL of that volume. The detection chamber (30) in this example has a height of 20 Ξm to accommodate one single layer of cells. FIG. 3 represents an image obtained with several stained leukocytes from this example. It will be appreciated that the dimensions of the connection conduit and detection chamber may be adjusted.

The metering (6) and downstream (70) chambers were designed in this example to accommodate 5 uL and 4 uL, respectively. In this example, a 1 uL cell free plasma was drained from the downstream chamber (70) through the siphon (71).

Embodiments of the device described herein are capable of determining both partial leukocyte counts and a haematocrit fraction of blood.

Although the embodiments described above are adapted for the processing of a blood sample, at least some of the above embodiments are suitable for processing any liquid sample, for example any liquid to be reacted with one or more reagents prior to imaging. Indeed, the described resuspension and other liquid handling mechanisms and structures are equally applicable to applications that do not involve imaging, for example, where the use of reagents is required on its own or in connection with other detection mechanisms.

For the avoidance of doubt, reference to a flow barrier valve refers to a connection conduit incorporating a surface tension barrier to provide an impediment to capillary driven flow. The surface tension barrier can be provided by any suitable arrangement, for example a sudden expansion or other geometrical design, or a surface treatment of all or a portion of the conduit.

The above description is made in respect of embodiments for imaging of samples, but the invention is equally applicable to other detection techniques, e.g. electrochemical detection of sample components, or liquid flow handling without subsequent detection.

Further embodiments are disclosed in the following clauses:
1. A method for quantitative measuring of blood leukocytes, characterized in that:
   Blood in inserted in a first chamber of a cartridge;
   Blood flows by capillary action from the first chamber in a fluidic structure into a second detection chamber, and;
   While blood flows in the said fluidic structure, there is a gradual resuspension of different reagents, consisting of at least a fraction of haemolysing agent and at least a fraction of staining agent
   Capturing images of lysed and stained blood in the said second detection chamber;
   Performing image cell segmentation and classification of leukocytes by comparison of obtained images of the lysed and stained blood in the said second detection chamber with pre-defined image properties thresholds.
2. A method according to clause 1, wherein the cartridge further comprises a blood metering chamber, and
   The said blood metering chamber is filled with blood by capillary action, while the cartridge is stopped;
   The cartridge is rotated and metered blood is moved by centrifugation from the said blood metering chamber into a said downstream chamber
   And haematocrit fraction is determined by optical imaging measurement of the interface between packed red cells and blood plasma in the said downstream chamber.
3. A method according to any preceding clause, wherein the cartridge further comprises a blood metering chamber, and
   The said blood metering chamber is filled with blood by capillary action, while the cartridge is stopped;
   The cartridge is rotated and metered blood is moved by centrifugation from the said blood metering chamber into a said downstream chamber
   A predefined volume of blood plasma is extracted from the said downstream chamber into other downstream parts of the cartridge for further analytical purposes.
4. And haematocrit fraction is determined by optical imaging measurement of the interface between packed red cells and blood plasma in the downstream chamber.
5. A device suitable for automated differential counts of stained leukocyte sub-populations within a blood sample, comprising:
   an inlet for blood sample insertion in the device;
   at least one detection chamber having predefined dimensions;
   at least one connection chamber having predefined dimensions;
   optical means for illuminating the detection chamber;
   optical means for image acquisition of the detection chamber;
characterized by
   at least one connection chamber linking the inlet to a detection chamber wherein the connection chamber contains at least two types of dry reagents comprising (i) a haemolysing agent for selective lysis of erythrocytes in the blood sample, (ii) a staining agent for selective stain of leukocytes in the blood sample;
   said dry reagents being stored in a predefined extension of the said connection chamber;
   said connection chamber comprising at least one reaction area by gradual resuspension of said dry reagents while the blood sample flows through the connection chamber into the detection chamber;
   cell segmentation and classification from said acquired images by optical and morphological properties of segmented cells;
   differential and/or absolute leukocyte counting from said classified cells.
5. A device according to clause 4 wherein said dry reagents being stored in at least two different positions and occupying predefined extensions of the connection chamber.
6. A device according to any of the preceding clauses wherein a stabilizer agent specific for leukocytes of the family of aldehyde-based fixatives, picric acid-based fixatives and polyoxyethylene-polyoxypropylene block copolymers is stored in dry form in the said connection chamber.
7. A device according to any of the preceding claims wherein a surfactant is added in dry form to the said connection chamber.
8. A device according to any of the preceding clauses wherein the said haemolysing agent is a saponin family reagent.

9. A device according to any of the preceding clauses wherein the said stain agent belongs to the family of H&E stains, Romanowsky stains, methacromatic stains or any combination thereof.
10. A device according to any of the previous clauses wherein the individual or mixture of said dry reagents are resuspended in a volatile solution dispensed in predefined extensions of the connection chamber and stored as dry reagents by means of evaporation.
11. A device according to any of the preceding clauses wherein the detection cavity is confined between two parallel planar surfaces with the distance between both surfaces defining a detection chamber depth not greater than 0.03 mm.
12. A device according to any of the preceding clauses wherein the volumetry of the connection chamber is defined by a width below 2 mm, a length above 10 mm and a depth between 0.02 mm and 1 mm.
13. A device according to any of the preceding clauses wherein blood sample flow from said inlet through connection and detection chambers is maintained solely by capillary drive flow.
14. A device according to any of the preceding clauses wherein at least one dimension of the connection chamber is below the smallest dimension of said inlet and at least one dimension of the detection chamber is below the smallest dimension of the connection chamber.
15. A device according to any of the preceding clauses wherein the blood sample flow from said inlet through connection and detection chambers is maintained by pressure drive flow exerted by means of an external pumping.
16. A device according to any of the preceding clauses wherein the blood sample flow from said inlet through connection and detection chambers is maintained by pressure drive flow exerted by means of a centrifugal force acting on the said blood sample.
17. A device according to any of the preceding clauses comprising the additional fluidic bodies:
   at least one metering chamber;
   at least one split feature embodied in the metering chamber;
   at least one downstream chamber;
   at least one overflow chamber;
   at least one waste chamber;
   at least one flow barrier valve;
characterized by
   A device according to clause 17 wherein said fluidic bodies were drawn in polar coordinates relative to an axis of revolution perpendicular to the plane containing said fluidic bodies;
18. A device according to any of the preceding clauses wherein the said air channels network comprises an air venting open connecting the microfluidic structures enclosed in the device to its exterior.
19. A device according to any of the preceding clauses wherein a metering chamber with a predefined volumetry share the said blood sample inlet with the said connection chamber.
20. A device according to any of the preceding clauses wherein at least one dimension of the metering chamber is below the smallest dimension of the said inlet.
21. A device according to any of the preceding clauses wherein dry anticoagulant is stored in the said metering chamber.
22. A device according to any of the preceding clauses wherein the metering chamber comprises at least two flow barriers with predefined dimensions that function as capillary valves.
23. A device according to any of the preceding clauses wherein filling of the metering chamber by the said blood sample loaded in the said inlet is driven solely by capillary means.
24. A device according to any of the preceding clauses wherein at least one of the said flow barriers operates as a venting port and at least one of the flow barriers connects the said metering chamber to at least one downstream chamber located radially outwardly relative to the said axis of revolution.
25. A device according to any of the preceding clauses wherein the volume of the downstream chamber is inferior to the volume of the said metering chamber.
26. A device according to any of the preceding clauses wherein the metering chamber comprises at least one section featuring a split point given that a loaded blood sample with a predetermined volume subjected to an external force normal to the said split point is forced to break into two independent volumes.
27. A device according to any of the preceding clauses wherein the said flow barrier valve connecting metering and downstream chambers breaks for a device rotating at a predetermined angular velocity relative to the said axis of revolution.
28. A device according to any of the preceding clauses wherein the flow of the blood sample from the metering chamber into the downstream chamber is maintained by means of a centrifugal force exerted to the said blood sample.
29. A device according to any of the preceding clauses wherein the said downstream chamber is connected to the said overflow chamber.
30. A device according to any of the preceding clauses wherein both downstream and overflow chambers are vented independently;
31. A device according to any of the preceding clauses wherein the blood sample comprised in both downstream and overflow chambers is subjected to a centrifugal force for a predetermine time resulting in a two-phase separation of said blood sample into sedimented erythrocytes and blood plasma supernatant.
32. A device according to any of the preceding clauses wherein the distance relative to the axis of revolution of the separation of the said sedimenting erythrocytes and blood plasma within both downstream and overflow chambers is measured by means of optical image acquisition as a function of time.
33. A device according to any of the preceding clauses wherein the length of each of the said blood plasma and erythrocyte enriched phases is measured in the radial direction relative to the axis of revolution as a function of time.
34. A device according to any of the preceding clauses wherein the said detection chamber is connected by at least one channel to the said waste chamber which is located in an inward radial position relative to the axis of revolution.
35. A device according to any of the preceding clauses wherein the said waste chamber comprises a capillary flow barrier at a predefined distance from the axis of rotation and at least one connection to the air channel network.

The invention is not limited to the specific embodiments disclosed above and many variations and modifications of the above disclosure are possible without departing from the scope of the appendant claims.

The invention claimed is:

1. A device for use in imaging a liquid sample, the device comprising:
   an inlet for accepting a sample into the device;
   a connection conduit;
   a detection chamber for optical detection of the sample;
   a metering chamber arranged to hold a predefined volume of the sample, wherein the metering chamber is in fluidic connection with the inlet and the connection conduit;
   a split feature arranged between the metering chamber and the connection conduit to split the sample between the metering chamber and the connection conduit; and
   a downstream chamber in fluidic connection with the metering, chamber and arranged to receive the predefined volume of the sample;
   wherein the connection conduit connects the inlet to the detection chamber,
   wherein the connection conduit contains one or more dry reagents for reaction with the sample as the sample passes through the connection conduit,
   wherein at least one dimension of the connection conduit is less than the smallest dimension of the inlet and at least one dimension of the detection chamber is less than the smallest dimension of the connection conduit,
   wherein the device is arranged for rotation about an axis of rotation to drive liquid flow to the downstream chamber, and
   wherein the split feature is arranged to separate a volume of the sample in the metering chamber from a volume of the sample in the connection conduit in response to the centrifugal force.

2. The device of claim 1, wherein the sample is a blood sample, the one or more dry reagents include a haemolysing agent for selective lysis of erythrocytes in the blood sample and a staining agent for selectively staining leukocytes in the blood sample.

3. The device of claim 1, wherein the connection conduit comprises a main conduit portion and one or more protrusions extending from the main conduit portion wherein the dry reagents are stored in the one or more protrusions and respective junction regions between the one or more protrusions and the main conduit portion provide a reaction region in which gradual resuspension of the dry reagents can occur.

4. The device of claim 3, wherein the protrusions comprise a main portion and a neck portion in the region of the junction, the neck portion having a smaller cross-sectional area along the main conduit portion than the main portion.

5. The device of claim 1, wherein the connection conduit is of a meandering configuration.

6. The device of claim 1, wherein the connection conduit further contains a stabilizer agent in dry form.

7. The device of claim 1, wherein the connection conduit further contains a surfactant in dry form.

8. The device of claim 1, further comprising an overflow chamber in fluidic connection with the downstream chamber and further comprising a siphon in fluidic connection with the downstream chamber, wherein an inlet of the siphon is arranged radially inwards from a portion of the downstream chamber such that when the device is subjected to a centrifugal force and the siphon is primed, a predetermined volume of the sample is siphoned from the sample in the downstream chamber.

9. The device of claim 1, wherein dry anticoagulant is stored in the metering chamber.

10. The device of claim 1, wherein the metering chamber comprises a surface tension barrier, the surface tension barrier being arranged to stop capillary driven flow between the metering chamber and the downstream chamber.

11. The device of claim 1, further comprising a waste chamber wherein the waste chamber is in fluidic connection with the detection chamber, and arranged radially inward from the detection chamber to receive centrifugally driven overflow from the detection chamber.

12. A system for imaging a sample comprising the device of claim 1, the system further comprising:
   an imager for acquiring at least one image of the sample in the detection chamber, the downstream chamber or both.

13. The system of claim 12, further comprising a drive for rotating the device.

14. The system of claim 12, further comprising a processor configured to process the at least one image of the sample in the detection chamber, when the sample is a blood sample, to segment stained cells in the image, the processor being further configured to determine a haematocrit fraction of the blood sample in the downstream chamber and, in the overflow chamber.

15. A method for imaging a liquid sample, the method comprising the steps of:
   inserting a sample into a first chamber of a cartridge;
   causing the sample to flow by capillary action from the first chamber through a connection conduit into a detection chamber;
   while the sample flows through the connection conduit gradually re-suspending one or more dry reagents in the sample
   filling a metering chamber with the sample by capillary action;
   rotating the cartridge to separate cellular material from blood plasma in the downstream chamber and imaging the sample in the downstream chamber once cellular material has been separated; and
   capturing at least one image of the sample in the detection chamber.

16. The method of claim 15, wherein the sample is a blood sample, the one or more dry reagents include a haemolysing agent for selective lysis of erythrocytes in the blood sample and a staining agent for selective stain of leukocytes in the blood sample.

17. The method of claim 16, further comprising performing image cell segmentation and classification of leukocytes by comparison of obtained images of the lysed and stained blood in the detection chamber with pre-defined image property thresholds.

18. The method of claim 15, wherein the first chamber and the metering chamber are filled from a common inlet.

19. The method of claim 15, further comprising rotating the cartridge to separate cellular material from blood plasma in the downstream chamber and imaging the sample in the downstream chamber once cellular material has been separated.

* * * * *